United States Patent
Heidl et al.

(10) Patent No.: US 11,591,367 B2
(45) Date of Patent: Feb. 28, 2023

(54) MELANOCORTIN-1-RECEPTOR AGONISTS

(71) Applicant: DSM IP ASSETS B.V., Heerlen (NL)

(72) Inventors: Marc Heidl, Kaiseraugst (CH); Eileen Jackson, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 529 days.

(21) Appl. No.: 16/338,758

(22) PCT Filed: Oct. 2, 2017

(86) PCT No.: PCT/EP2017/074937
§ 371 (c)(1),
(2) Date: Apr. 2, 2019

(87) PCT Pub. No.: WO2018/065345
PCT Pub. Date: Apr. 12, 2018

(65) Prior Publication Data
US 2021/0277058 A1    Sep. 9, 2021

(30) Foreign Application Priority Data
Oct. 4, 2016 (EP) .................................. 16192138

(51) Int. Cl.
| | | |
|---|---|---|
| *C07K 7/06* | (2006.01) | |
| *A61K 8/64* | (2006.01) | |
| *A61Q 19/10* | (2006.01) | |
| *A61K 8/23* | (2006.01) | |
| *A61K 8/25* | (2006.01) | |
| *A61K 8/27* | (2006.01) | |
| *A61K 8/29* | (2006.01) | |
| *A61K 8/34* | (2006.01) | |
| *A61Q 19/04* | (2006.01) | |

(52) U.S. Cl.
CPC .................. *C07K 7/06* (2013.01); *A61K 8/23* (2013.01); *A61K 8/25* (2013.01); *A61K 8/27* (2013.01); *A61K 8/29* (2013.01); *A61K 8/34* (2013.01); *A61K 8/64* (2013.01); *A61Q 19/04* (2013.01)

(58) Field of Classification Search
CPC combination set(s) only.
See application file for complete search history.

(56) References Cited

U.S. PATENT DOCUMENTS

| | | | |
|---|---|---|---|
| 2005/0142078 A1* | 6/2005 | Dorr ...................... | A61K 38/34 424/59 |
| 2009/0297444 A1 | 12/2009 | Perricone et al. | |
| 2010/0310484 A1* | 12/2010 | Hocquaux ................ | A61K 8/64 530/331 |
| 2012/0225831 A1 | 9/2012 | Yang et al. | |

FOREIGN PATENT DOCUMENTS

| | | | |
|---|---|---|---|
| JP | 2011-521949 | 7/2011 | |
| JP | 2013-511554 | 4/2013 | |
| WO | WO-2005009402 A2 * | 2/2005 | ............... A61K 8/37 |
| WO | 2011/063367 | 5/2011 | |
| WO | WO 2014/081845 | 5/2014 | |

OTHER PUBLICATIONS

English translation of Hocquaux et al. (WO 2005009402)—generated by USPTO library Jun. 14, 2021. 5 pages. (Year: 2005).*
Betts et al,. "Amino Acid Properties and Consequences of Substitutions," Bioinformatics for Geneticists, chtpr 14, Eds. Barnes and Gray, Publ. John Wiley & Sons, Ltd., pp. 289-316 (2003) (Year: 2003).*
International Search Report for PCT/EP2017/074937, dated Dec. 12, 2017, 4 pages.
Written Opinion of the ISA for PCT/EP2017/074937, dated Dec. 12, 2017, 6 pages.
Hruby et al., "Alpha-Melanotropin: The Minimal Active Sequence In The Frog Skin Bioassay", Journal of Medicinal Chemistry, American Chemical Society, vol. 30, No. 11, Jan. 1, 1987, pp. 2126-2130.
Haskell-Luevano et al., "Characterization of Melanocortin NDP-MSH Agonist Peptide Fragments At The Mouse Central And Peripheral Melanocortin Receptors", Journal of Medicinal Chemistry, American Chemical Society, vol. 44, No. 13, Jan. 1, 2001, pp. 2247-2252.
Prusis, Peteris et al, "*Design of new small cyclic melanocortin receptor-binding peptides using molecular modelling: Role of the His residue in the melanocortin peptide core*", European Journal of Medicinal Chemistry, vol. 36, pp. 137-146 (2001).
Holder, Jerry Ryan et al, "Characterization of aliphatic, cyclic, and aromatic N-terminally "capped" His-D-Phe-Arg-Trp-NH$_2$ *tetrapeptides at the melanocortin receptors*", European Journal of Pharmacology, vol. 462, pp. 41-52 (2003).

* cited by examiner

*Primary Examiner* — Julie Ha
*Assistant Examiner* — Kristina M Hellman
(74) *Attorney, Agent, or Firm* — Nixon & Vanderhye P.C.

(57) ABSTRACT

The present invention relates to novel selective melanocortin-1 receptor (MC1R) agonists as well as the use thereof as skin tanning agents.

10 Claims, No Drawings

MELANOCORTIN-1-RECEPTOR AGONISTS

This application is the U.S. national phase of International Application No. PCT/EP2017/074937 file 2 Oct. 2017, which designated the U.S. and claims priority to EP Patent Application No. 16192138.2 filed 4 Oct. 2016, the entire contents of each of which are hereby incorporated by reference.

The present invention relates to novel selective melanocortin-1 receptor (MC1R) agonists as well as the use thereof as skin tanning agents.

Ultraviolet-light (UV)-induced tanning is based on a complex multistep transformation of L-tyrosine to melanin which includes MC1R, a G protein coupled receptor expressed on the surface of melanocytes. MC1R is up-regulated by the MC1R agonist α-melatropin, an α-melanocyte stimulating hormone (α-MSH), which production is induced by UV-light. Binding of this agonist to MC1R triggers the melanogenic cascade that starts with the activation of adenylate cyclase that results in the stimulation of cyclic adenosine monophosphate (cAMP) synthesis, activation of the cAMP-dependent protein kinase A (PKA) and then a series of reactions that finally result in the increased synthesis of melanin and thus in an increased skin tan. Such natural, UV-light induced tanning, however, is not always desirable, as the exposure to UV radiation may also cause skin damages such as increased wrinkling, elastosis, pigmentary changes as well as precancerous and cancerous skin lesions.

Thus, it is desirable to have an alternative to natural tanning. Therefore, self-tanning ingredients are gaining more importance for various applications in the skin and sun care market.

The majority of cosmetic products for the artificial tanning of the skin are based on carbonyl derivatives which permit the formation of colored compounds by interaction with the amino acids of the skin. These compounds include mono- or polycarbonyl compounds, such as, for example, isatin, alloxan, ninhydrin, glyceraldehyde, mesotartaric aldehyde, glutaraldehyde, erythrulose and dihydroxyacetone (DHA). The skin tan obtained therewith is, however, often inhomogeneous and thus leads to blotchy skin which is highly unwanted by the consumer.

Thus, there is an ongoing need for alternative skin tanning agents such as in particular for MC1R agonists which effectively up-regulate MC1R while being readily and economically accessible to the cosmetic industry.

Surprisingly it has been found that compounds of formula (I), respectively a cosmetically acceptable salt thereof.

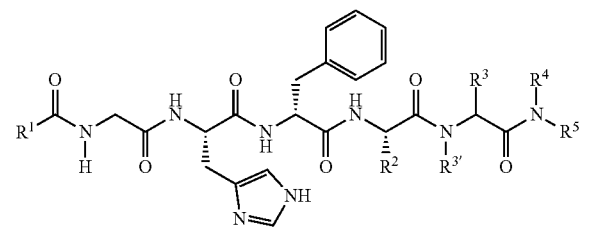

(I)

wherein
$R^1$ is are selected from the group consisting of a $C_1$-$C_{10}$ alkyl group, a $C_3$-$C_6$ cycloalkyl group, an aryl group or an aryl $C_1$-$C_6$ alkyl group;

$R^2$ is an amino acid side chain of a basic amino acid or an amino acid side chain of a 2-amino $C_{2-8}$ alkanoic acid;

$R^3$ and $R^{3'}$ are selected from the group consisting of H, an arylC$_1$-C$_6$ alkyl group or a heteroarylC$_1$-C$_6$ alkyl group, wherein the aryl respectively the heteroaryl can optionally be substituted, $R^4$ and $R^5$ are, independently of each other, H or a $C_1$-$C_{10}$ alkyl group; and with the proviso that only one of $R^3$ or $R^{3'}$ is H and the respective other one of $R^3$ and $R^{3'}$ is not H are highly efficient MC1R agonist and thus particularly suitable for the incorporation into cosmetic compositions suitable for skin tanning.

Thus, in a first aspect, the present invention relates to a compound of formula (I) or a cosmetically acceptable salt of a compound of formula (I)

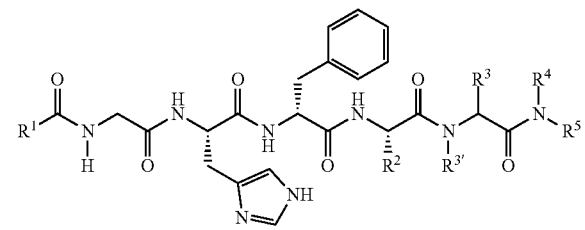

(I)

wherein
$R^1$ is are selected from the group consisting of a $C_1$-$C_{10}$ alkyl group, a $C_3$-$C_6$ cycloalkyl group, an aryl group or an arylC$_1$-C$_6$ alkyl group,
preferably $R^1$ is selected from the group consisting of a $C_1$-$C_2$ alkyl group, a $C_5$-$C_{12}$ aryl group or a benzyl group, most preferably of methyl or phenyl;

$R^2$ is an amino acid side chain of a basic amino acid or an amino acid side chain of a 2-amino $C_{2-8}$ alkanoic acid,
preferably $R^2$ is the amino acid side chain of arginine, 2,4-diaminobutyric acid or 2-aminohexanoic acid, most preferably of arginine or 2,4-diaminobutyric acid;

$R^3$ and $R^{3'}$ are selected from the group consisting of H, an arylC$_1$-C$_6$ alkyl group and a heteroarylC$_1$-C$_6$ alkyl group, wherein the aryl respectively the heteroaryl can optionally be substituted,
preferably $R^3$ and $R^{3'}$ are selected from the group consisting of H, an unsubstituted aryl(m)ethyl group and an unsubstituted heteroaryl(m)ethyl group, most preferably $R^3$ is selected from the group consisting of H, phenylmethyl, naphthylmethyl and (1H-indol-3-yl)methyl and $R^{3'}$ is H or (1H-indol-3-yl)ethyl;

$R^4$ and $R^5$ are, independently of each other, H or a $C_1$-$C_{10}$ alkyl group,
preferably $R^4$ and $R^5$ are, independently of each other, H or a $C_3$-$C_8$ alkyl group, most preferably H, propyl or octyl; and with the proviso that only one of $R^3$ or $R^{3'}$ is H and the respective other one of $R^3$ and $R^{3'}$ is not H (but the respective arylC$_1$-C$_6$ alkyl group or heteroarylC$_1$-C$_6$ alkyl group, with all the definitions and preferences as given herein for $R^3$ and $R^{3'}$).

The term '$C_x$-$C_y$alkyl group' refers to unbranched $C_x$-$C_y$alkyl or branched $C_3$-$C_y$alkyl groups such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and 3,5,5-trimethylhexyl groups.

The term '$C_3$-$C_6$cycloalkyl group' refers to a saturated, 3 to 6 membered hydrocarbon ring such as cyclopropyl, cyclobutyl, cyclopentyl and cyclohexyl. Preferably in all embodiments of the present invention the $C_3$-$C_6$cycloalkyl group is cyclopropyl, cyclopentyl or cyclohexyl, most preferably cyclohexyl.

The term "aryl" as used herein refers to an aromatic substituent containing 5 to 15 carbon atoms and containing a single aromatic ring or multiple aromatic rings which are fused together, directly linked or indirectly linked (such that the different aromatic rings are bound to a common group such as a methylene or ethylene group). Particularly advantageous aryl groups according to the present invention contain 6 to 12 carbon atoms containing a single aromatic ring or multiple aromatic rings which are fused together or directly linked. Most preferred aryl residues in all embodiments of the present invention are phenyl, naphtyl and biphenyl.

The term "side chain" of an amino acid refers to that portion of the amino acid attached to the common

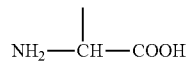

backbone of the respective amino acids. For instance, the side chain of serine is —$CH_2$—OH and the side chain of alanine is —$CH_3$.

The term "basic amino acid" as used herein refers to any natural or unnatural amino acid that have basic side chains at neutral pH such as the natural occurring amino acids arginine (Arg), lysine (Lys), and histidine (His) as well as the unnatural amino acids 2,4-diaminobutyric acid, homolysine and ornithine without being limited thereto. Advantageous amino acid side in all embodiments of the present invention are the side chains of arginine, lysine, 2,4-diaminobutyric acid, homolysine and ornithine such as in particular the side chains of arginine and 2,4-diaminobutyaric acid.

The term "2-amino $C_{2-8}$alkanoic acid" refers to amino acids

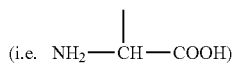

having a $C_{2-8}$ alkyl side chain, preferably a linear $C_{4-7}$ alkyl side chain. Most preferred 2-amino $C_{2-8}$ alkanoic acids in all embodiments of the present invention are 2-amino butanoic acid, 2-amino pentanoic acid, 2-amino hexanoic acid or 2-amino heptanoic acid such as in particular 2-amino hexanoic acid.

The term "aryl$C_1$-$C_6$ alkyl group" as used herein refers to a —$C_1$-$C_6$ alkyl-aryl group (i.e. to a $C_1$-$C_6$alkyl group which is substituted by an aryl group, i.e. the attachment point is the alkyl group), wherein the term "aryl" is as defined above. Advantageous aryl$C_1$-$C_6$ alkyl groups are aryl$C_1$-$C_2$ alkyl groups such as in particular phenyl(m)ethyl or naphthyl(m)ethyl, such as most preferably phenylmethyl (i.e. benzyl).

The term 'heteroaryl$C_1$-$C_6$ alkyl group' refers to a —$C_1$-$C_6$ alkyl-heteroaryl (i.e. to a $C_1$-$C_6$alkyl group which is substituted by a heteroaryl group, i.e. the attachment point is the alkyl group), wherein the term "heteroaryl" refers to a 5- or 6-membered aromatic ring containing one or more heteroatoms, viz., N, O or S; these heteroaromatic rings may be fused to other aromatic systems. Particularly preferred heteroaromatic rings encompass indole, pyridine and quinoline. In all embodiments of the present invention preferred heteroaryl$C_1$-$C_6$ alkyl group are heteroaryl$C_1$-$C_2$alkyl groups such as (1H-indol-3-yl)(m)ethyl, (pyridin-2-yl)(m)ethyl, (pyridin-3-yl)(m)ethyl, (quinolin-2-yl)(m)ethyl and (quinolin-3-yl)(m)ethyl groups.

The aromatic aryl respectively heteroaryl residues may, independently of each other, be unsubstituted or substituted with one or more substituents. In all embodiments of the present invention, such substituents are preferably selected from halogen, hydroxy, nitro, cyano, $C_1$-$C_6$ alkyl, $C_1$-$C_6$ alkoxy and $C_1$-$C_6$ alkanoyloxy. More preferably in all embodiments of the present invention the aryl respectively heteroaryl residues are, independently of each other, unsubstituted or substituted with one substituent selected from the group consisting of F, Cl, hydroxy, cyano, $C_1$-$C_3$ alkyl, $C_1$-$C_3$ alkoxy and $C_1$-$C_3$alkanoyloxy such as in particular unsubstituted or substituted with one substituent selected from the group consisting of F or hydroxy. Most preferably, in all embodiments of the present invention, the aryl and the heteroaryl residues are unsubstituted.

In all embodiments of the present invention particular preferred heteroaryl$C_1$-$C_2$ alkyl groups are (1H-indol-3-yl)(m)ethyl, 5-fluoro(1H-indol-3-yl)(m)ethyl, 6-fluoro(1H-indol-3-yl)(m)ethyl, 5-hydroxy(1H-indol-3-yl)(m)ethyl, (pyridin-2-yl)(m)ethyl, (pyridin-3-yl)(m)ethyl, (quinolin-2-yl)(m)ethyl and (quinolin-3-yl)(m)ethyl. Most preferred in all embodiments of the present invention are the heteroaryl$C_1$ alkyl groups (1H-indol-3-yl)methyl, 5-fluoro(1H-indol-3-yl)methyl, 6-fluoro(1H-indol-3-yl)8m)ethyl, 5-hydroxy(1H-indol-3-yl)methyl, (pyridin-2-yl)methyl, (pyridin-3-yl)methyl, (quinolin-2-yl)methyl and (quinolin-3-yl)methyl and the heteroaryl$C_2$ alkyl groups (1H-indol-3-yl)ethyl such as in particular (1H-indol-3-yl)methyl and (1H-indol-3-yl)ethyl.

It is well understood, that the present invention encompasses the compounds of formula (I) as optically pure isomers such as e.g. as pure enantiomers or stereoisomers as well as mixtures of different isomers such as e.g. as racemates, or mixtures of diastereoisomers.

The term 'or a cosmetically acceptable salt of compound of formula (I)' respectively "or a cosmetically acceptable salt thereof" refers to compounds of formula (I) in the form of an acid addition salt such as in the form of a chloride, an acetate or a trifluoroacetate salt. Alternatively, the salt may be formed by reaction with an alkali or earth alkaline base resulting in the respective alkali or earth alkaline salt such as in particular the respective lithium, sodium, potassium, magnesium or calcium salts.

Most preferred, in all embodiments of the present invention, are the compounds of formula (I) as such or in the form of their acetates or trifluoroacetates (i.e. as 2,2,2-trifluoroacetates). Such salts are easily prepared by a person skilled in the art.

In a particular advantageous embodiment, the present invention relates to compounds of formula (I) respectively a cosmetically acceptable salt thereof such as in particular the acetate or trifluoroacetate salt thereof, wherein $R^1$ is a $C_1$-$C_2$ alkyl group or a $C_6$-$C_{12}$ aryl group;
$R^2$ is an amino acid side chain of a basic amino acid;
$R^3$ and $R^{3'}$ are selected from the group consisting of H, an unsubstituted aryl(m)ethyl group or an unsubstituted heteroaryl(m)ethyl group; and
$R^4$ and $R^5$ are, independently of each other H or a $C_1$-$C_{10}$alkyl group; and
with the proviso that only one of $R^3$ or $R^{3'}$ is H and the respective other one of $R^3$ and $R^{3'}$ is not H.

Even more advantageous compounds of formula (I) or cosmetically acceptable salts thereof such as in particular the trifluoroacetate salt thereof in all embodiments of the present invention are the ones, wherein $R^1$ is phenyl;
$R^2$ is the amino acid side chain of arginine or 2,4-diaminobutyric acid;
$R^3$ is H, phenylmethyl, naphthylmethyl or (1H-indol-3-yl)methyl and $R^{3'}$ is H or (1H-indol-3-yl)ethyl;
$R^4$ and $R^5$ are, independently of each other H, propyl or octyl; and
with the proviso that only one of $R^3$ or $R^{3'}$ is H and the respective other one of $R^3$ and $R^{3'}$ is not H.

Most preferred in all embodiments according to the present invention are the compounds as listed in table 1, respectively the respective trifluoroacetate salts thereof:

TABLE 1

| # | Structure | Notation based on amino acid sequence* |
|---|-----------|----------------------------------------|
|   | 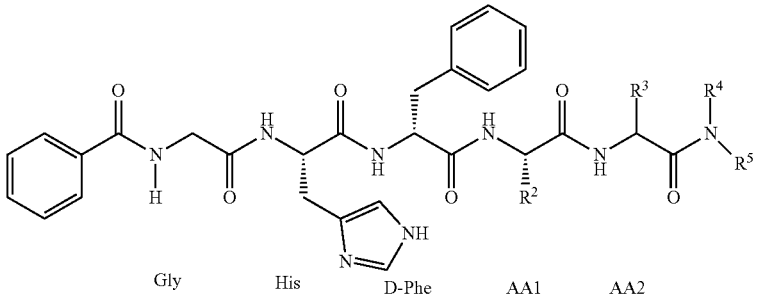 | Bz-Gly-His-DPhe-AA1-AA2-NR⁴R⁵ |
| (I-a) | 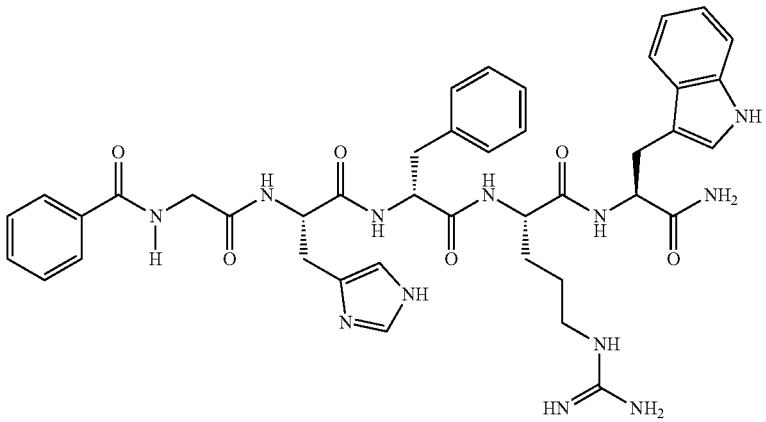 [SMILES: N=C(N)NCCC[C@H](NC(=O)[C@@H](Cc1ccccc1)NC(=O)[C@H](Cc1c[nH]cn1)NC(=O)CNC(=O)c1ccccc1)C(=O)N[C@@H](Cc1c[nH]c2ccccc12)C(N)=O] | Bz-Gly-His-D-Phe-Arg-Trp-NH₂ |
| (I-b) | 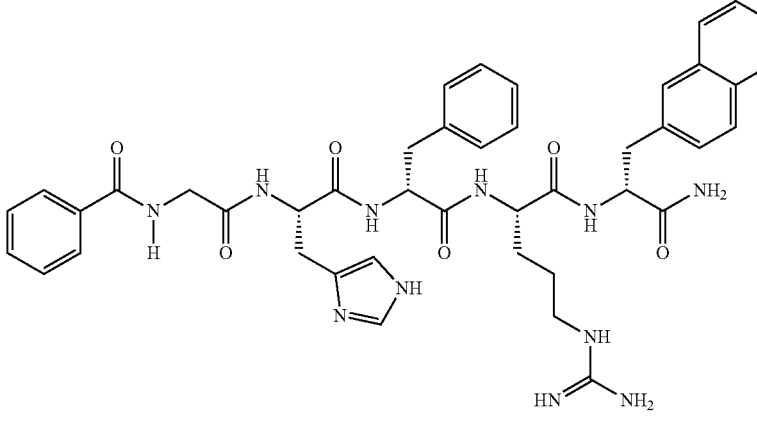 | Bz-Gly-His-D-Phe-Arg-D-2-NaphAla-NH₂ |

TABLE 1-continued

| # | Structure | Notation based on amino acid sequence* |
|---|---|---|
| (I-c) | 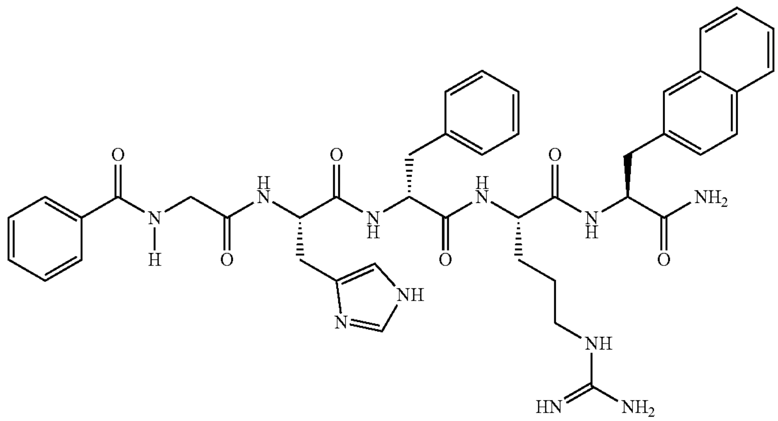 [SMILES: N=C(N)NCCC[C@H](NC(=O)[C@@H](Cc1ccccc1)NC(=O)[C@H](Cc1c[nH]cn1)NC(=O)CNC(=O)c1ccccc1)C(=O)N[C@@H](Cc1ccc2ccccc2c1)C(N)=O] | Bz-Gly-His-D-Phe-Arg-L-2-NaphAla-NH$_2$ |
| (I-d) | 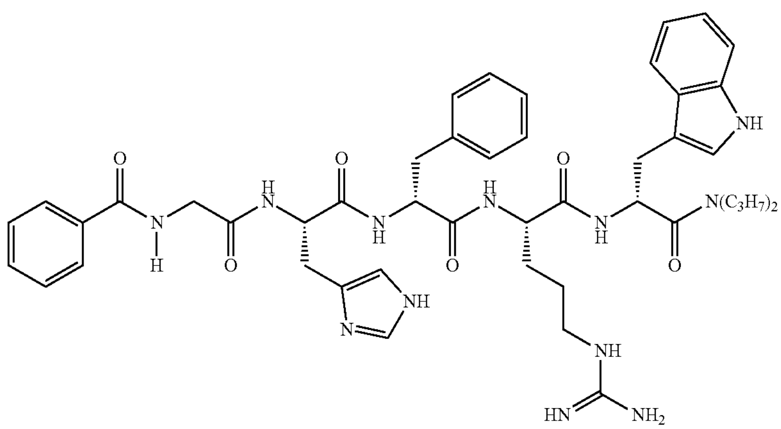 | Bz-Gly-His-D-Phe-Arg-D-Trp-N(Propyl)$_2$ |
| (I-e) | 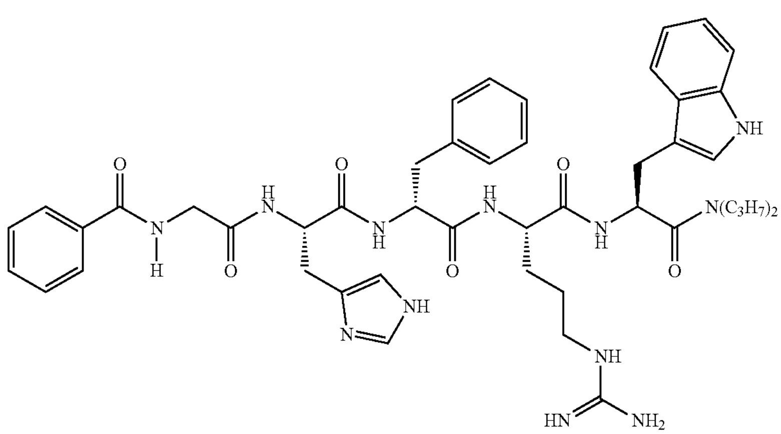 | Bz-Gly-His-D-Phe-Arg-Trp-N(Propyl)$_2$ |

TABLE 1-continued

| # | Structure | Notation based on amino acid sequence* |
|---|---|---|
| (I-f) | 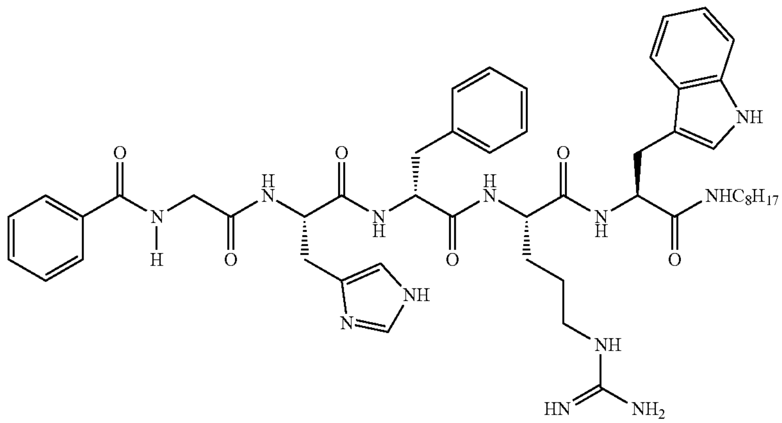 | Bz-Gly-His-D-Phe-Arg-Trp-NHOctyl |
| (I-g) | 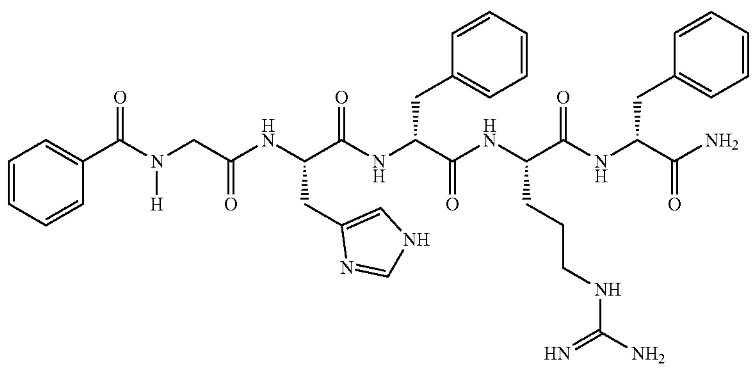 [SMILES: N=C(N)NCCC[C@H](NC(=O)[C@@H](Cc1ccccc1)NC(=O)[C@H](Cc1c[nH]cn1)NC(=O)CNC(=O)c1ccccc1)C(=O)N[C@H](Cc1ccccc1)C(N)=O] | Bz-Gly-His-D-Phe-Arg-D-Phe-NH₂ |
| (I-h) | 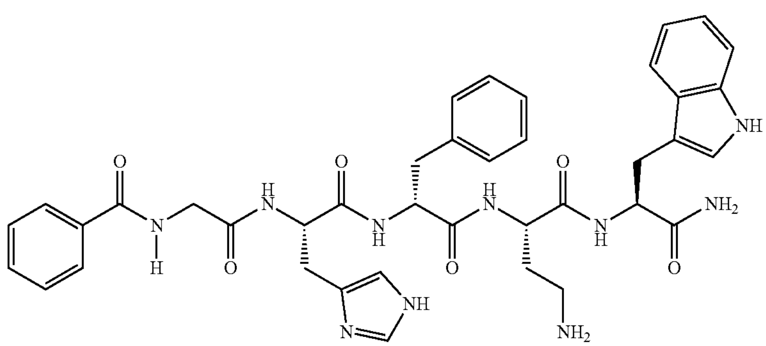 [SMILES: NCC[C@H](NC(=O)[C@@H](Cc1ccccc1)NC(=O)[C@H](Cc1c[nH]cn1)NC(=O)CNC(=O)c1ccccc1)C(=O)N[C@@H](Cc1c[nH]c2ccccc12)C(N)=O] | Bz-Gly-His-D-Phe-Dab-Trp-NH₂ |
| (I-i) | 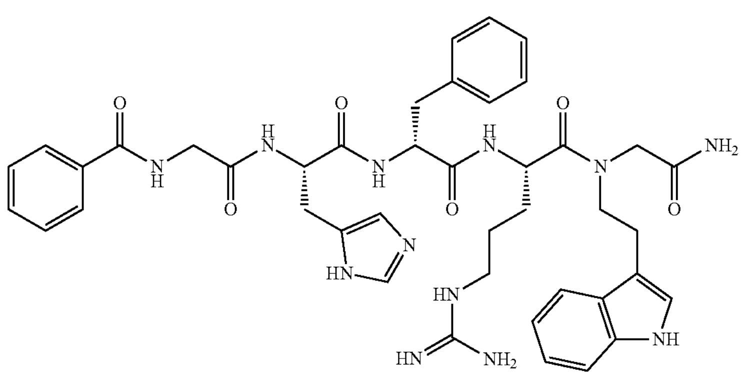 [SMILES: N=C(N)NCCC[C@H](NC(=O)[C@@H](Cc1ccccc1)NC(=O)[C@H](Cc1cnc[nH]1)NC(=O)CNC(=O)c1ccccc1)C(=O)N(CCc1c[nH]c2ccccc12)CC(N)=O] | Bz-Gly-His-D-Phe-Arg-(N-IndEt)Gly-NH₂ *2TFA |

The compounds according to the present invention may be prepared by methods standard in peptide chemistry as illustrated in the examples.

In yet another embodiment the present invention relates to the use of a compound of formula (I) or a cosmetically acceptable salt thereof with all the definitions and preferences as given herein as MC1R agonist and in particular for stimulating the melanin production and/or increasing the melanin content in human skin.

Furthermore, the present invention relates to the use of a compound of formula (I) or a cosmetically acceptable salt thereof with all the definitions and preference as given as self-tanning agent or artificial/sunless tanning agent.

As self-tanning respectively artificial/sunless tanning agent, the compounds according to the present invention are particular suitable for browning of human skin, for imparting an appearance similar to natural tanning of the skin, for the enhancement of the natural glow of the skin, for the protection of skin against UV-radiation, for the prevention of photoage-induced skin structure defects such as wrinkles and fine lines and/or for providing a healthy appearance.

The term "self-tanning agent" or "artificial/sun-less tanning agent" refers to agents which, when topically applied onto the skin, in particular onto the face, elicit a tanning effect with an appearance more or less similar to that resulting from prolonged exposure to the sun (natural tanning) or under a UV lamp.

Such self-tanning agents or artificial/sun-less tanning agents are preferably applied topically in the form of a cosmetic composition. Thus, in another embodiment, the invention relates to a cosmetic composition comprising at least one compound of formula (I) or a cosmetically acceptable salt thereof and a cosmetically acceptable carrier.

In particular, these cosmetic compositions are compositions intended for artificial/sunless tanning and/or browning of human skin, for imparting an appearance similar to natural tanning of the skin, for the enhancement of the natural glow of the skin, for the protection of skin against UV-radiation, for the prevention of photoage-induced skin structure defects such as wrinkles and fine lines and/or for providing a healthy appearance (i.e. self-tanning compositions).

The amount of the compound of formula (I) in the cosmetic composition can easily be adjusted by a person skilled in the art in order to achieve the desired beneficial effect. Preferably, the amount of the compound of formula (I) in the cosmetic compositions according to the present invention is at least 1 ppm based on the total weight of the cosmetic composition. In all embodiments of the present invention the amount of the compound of formula (I) is preferably selected in the range of about 0.00001 to 0.5 wt.-%, more preferably in the range of 0.0001 to 0.25 wt.-%, most preferably in the range of 0.0001 to 0.1 wt.-% based on the total weight of the cosmetic composition.

The present invention also relates to a method for artificially tanning and/or browning of the skin, said method comprising the step of topically applying a cosmetic composition according to the present invention with all the definitions and preferences given herein to the skin.

The invention also relates to a method for artificially tanning and/or browning the skin, said method comprising the step of topically applying an effective amount of a cosmetic composition according to the present invention with all the definitions and preferences given herein on the skin for such a period of time as is required to elicit the desired artificial/sunless tanning effect.

The term 'effective amount' as used herein refers to an amount necessary to obtain a physiological effect. The physiological effect may be achieved by one single dose or by repeated doses. The dosage administered may, of course, vary depending upon known factors, such as the physiological characteristics of the particular composition and its mode and route of administration; the age, health and weight of the recipient; the nature and extent of the symptoms; the kind of concurrent treatment; the frequency of treatment; and the effect desired and can be adjusted by a person skilled in the art.

Thus, the amount of the cosmetic composition to be applied to the skin is not critical and can easily be adjusted by a person skilled in the art. Preferably the amount is selected in the range of 0.1 to 3 mg/cm$^2$ skin, such as preferably in the range of 0.1 to 2 mg/cm$^2$ skin and most preferably in the range of 0.5 to 2 mg/cm$^2$ skin.

The term 'cosmetic composition' refers to compositions which are used to treat, care for or improve the appearance of the skin and/or the scalp. Particular advantageous cosmetic compositions according to the present invention are skin care compositions.

Preferred cosmetic compositions according to the present invention are compositions for artificial/sunless tanning and/or browning of human skin, sunscreen compositions or moisturizers.

The cosmetic compositions according to the invention are preferably intended for topical application, which is to be understood as the external application to keratinous substances, such as in particular the skin.

The term 'cosmetically acceptable carrier' as used herein refers to a physiologically acceptable medium which is compatible with keratinous substances. Suitable carriers are well known in the art and are selected based on the end-use application. Preferably, the carriers of the present invention are suitable for application to skin (e.g., sunscreens, creams, milks, lotions, masks, serums, hydrodispersions, foundations, creams, creamgels, or gels etc.). Such carriers are well-known to one of ordinary skill in the art, and can include one or more compatible liquid or solid filler diluent, excipient, additive or vehicle which are suitable for application to skin. The exact amount of carrier will depend upon the level of the compound of formula (I) and any other optional ingredients that one of ordinary skill in the art would classify as distinct from the carrier (e.g., other active components). The compositions of the present invention preferably comprise from about 75% to about 99.999%, more preferably from about 85% to about 99.99%, still more preferably from 90% to about 99%, and most preferably, from about 93% to about 98%, by weight of the composition, of a carrier.

The cosmetic compositions of the present invention can be formulated into a wide variety of product types, including creams, waxes, pastes, lotions, milks, mousses, gels, oils, tonics, and sprays. Preferably the compounds of formula (I) are formulated into lotions, creams, gels, and tonics. These product forms may be used for a number of applications, including, but not limited to, hand and body lotions, facial moisturizers, anti-ageing preparations, make-ups including foundations, and the like. Any additional components required to formulate such products vary with product type and can be routinely chosen by one skilled in the art.

If compositions of the present invention are formulated as an aerosol and applied to the skin as a spray-on product, a propellant is added to the composition.

The cosmetic compositions according to the present invention can be prepared by conventional methods in the art such as e.g. by admixing a compound of formula (I) with all the definitions and preferences given herein with the cosmetically acceptable carrier. The cosmetic compositions of the invention (including the carrier) may comprise further conventional cosmetic adjuvants and additives, such as preservatives/antioxidants, fatty substances/oils, water, organic solvents, silicones, thickeners, softeners, emulsifiers, antifoaming agents, aesthetic components such as fragrances, surfactants, fillers, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

In accordance with the present invention, the cosmetic compositions according to the invention may also comprise further cosmetically active ingredients conventionally used in cosmetic compositions. Exemplary active ingredients encompass further self-tanning agents, UV-filters, agents for the treatment of hyperpigmentation; agents for the prevention or reduction of inflammation; firming, moisturizing, soothing, and/or energizing agents as well as agents to improve elasticity and skin barrier.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council accessible by the online INFO BASE without being limited thereto.

The necessary amounts of the active ingredients as well as the cosmetic excipients, diluents, adjuvants, additives etc. can, based on the desired product form and application, easily be determined by the skilled person. The additional ingredients can either be added to the oily phase, the aqueous phase or separately as deemed appropriate.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

The compositions according to this invention can additionally comprise further organic or inorganic UV-filter substances (light screening agents) which are active in the UV-A and/or UV-B regions (absorbers), such UV-filter substances being water-soluble, fat-soluble or insoluble in commonly used cosmetic solvents.

Exemplary UVA, UVB and/or broadspectrum UV-filter substances encompass dibenzoylmethane derivatives such as e.g. butyl methoxydibenzoylmethane (PARSOL® 1789); acrylates such as e.g. octocrylene (PARSOL® 340); camphor derivatives such as e.g. 4-methyl benzylidene camphor (PARSOL® 5000) or terephthalylidene dicamphor sulfonic acid (Mexoryl® SX); cinnamate derivatives such as e.g. ethylhexyl methoxycinnamate (PARSOL® MCX) or isoamyl methoxycinnamate; p-aminobenzoic acid derivatives such as e.g. p-aminobenzoic acid or 2-ethylhexyl p-dimethylaminobenzoate; benzophenones such as e.g. benzophenone-3, benzophenone-4, 2,2',4,4'-tetrahydroxy-benzophenone or 2,2'-dihydroxy-4,4'-dimethoxybenzophenone; esters of benzalmalonic acid such as e.g. di-(2-ethylhexyl) 4-methoxybenzalmalonate; organosiloxane compounds carrying chromophore groups such as e.g. polysilicone-15 (PARSOL® SLX) or drometrizole trisiloxane (Mexoryl® XL); imidazole derivatives such as e.g. 2-phenyl benzimidazole sulfonic acid and salts thereof such as e.g. its sodium- or potassium salts (PARSOL® HS); salicylate derivatives such as e.g. ethylhexyl salicylate (PARSOL® EHS, Neo Heliopan® OS), isooctyl salicylate or homosalate (PARSOL® HMS, Neo Heliopan® HMS); triazine derivatives such as e.g. ethylhexyl triazone (Uvinul® T-150), diethylhexyl butamido triazone (Uvasorb© HEB), bis-ethylhexyloxyphenol methoxyphenyl triazine (Tinosorb® S) or Tris-Biphenyl Triazine (2,4,6-Tris(biphenyl-4-yl)-1,3,5-triazin, Tinosorb® A2B); Benzotriazole derivatives such as e.g. methylene bis-benzotriazolyl tetramethylbutylphenol (Tinosorb® M); encapsulated UV-filters such as e.g. encapsulated ethylhexyl methoxycinnamate (Eusolex® UV-pearls); amino substituted hydroxybenzophenones such as e.g. diethylamino hydroxybenzoyl hexyl benzoate (Aminobenzophenon, Uvinul® A Plus); benzoxazol-derivatives such as e.g. 2,4-bis-[5-1(dimethylpropyl)benzoxazol-2-yl-(4-phenyl)-imino]-6-(2-ethylhexyl)-imino-1,3,5-triazin (Uvasorb® K2A); phenylene-1,4-bis-benzimidazolsulfonic acids or salts thereof such as e.g. disodium phenyl dibenzimidazole tetrasulfonate (2,2-(1,4-phenylene)bis-(1H-benzimidazol-4, 6-disulfonic acid, Neoheliopan® AP); 1,1'-(1,4-piperazinediyl)bis[1-[4-(diethylamino)-2-hydroxybenzoyl]phenyl]-methanone (CAS No. 919803-06-6); as well as Bis (butylbenzoate) diaminotriazine aminopropyltrisiloxane (CAS No. 207562-42-3).

Inorganic UV-filter substances encompass pigments such as e.g. microparticulated zinc oxide or titanium dioxide (e.g. commercially available as PARSOL® TX) The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

Preferred UVB-filter substances to be incorporated into the cosmetic compositions according to the invention encompass polysilicone-15, phenylbenzimidazol sulfonic acid, octocrylene, ethylhexyl methoxycinnamate, ethyl hexylsalicylate, tris-biphenyl triazine and/or homosalate.

Preferred broadband UV-filter substances to be incorporated into the cosmetic compositions according to the invention encompass unsymmetrical s-triazine derivatives such as in particular bis-ethylhexyloxyphenol methoxyphenyl triazine, certain benzophenones such as e.g. 2-hydroxy-4-methoxy-benzophenon, methylene bis-benzotriazolyl tetramethylbutylphenol and/or titanium dioxide.

Preferred UVA-filter substances to be incorporated into the cosmetic compositions according to the invention encompass butyl methoxydibenzoylmethane, diethylamino hydroxybenzoyl hexyl benzoate, 2, 4-bis-[5-1(dimethylpropyl)benzoxazol-2-yl-(4-phenyl)-imino]-6-(2-ethylhexyl)-imino-1,3,5-triazine and/or disodium phenyl dibenzimidazole tetrasulfonate, in particular butyl methoxydibenzoylmethane and/or diethylamino hydroxybenzoyl hexyl benzoate.

If the topical sunscreen emulsions comprise butyl methoxydibenzoylmethane, then they advantageously contain in addition at least one suitable photostabilizer for butyl methoxydibenzoylmethane. Besides specific UV-filters listed above which are known to a person skilled in the art to be able to photostabilize butyl methoxydibenzoylmethane, further exemplary photostabilizers encompass Polyester 8 (Polycrylene®); Methoxycrylene (Solastay); diethylhexyl syringylidene malonate (Oxynex ST liquid); diethylhexyl naphthalate (Corapan TQ) as well as Benzotriazolyl Dodecyl p-Cresol (Tinogard® TL) without being limited thereto. An overview on such photostabilizers is e.g. given in 'SPF Boosters & Photostability of Ultraviolet Filters', HAPPI, October 2007, p. 77-83 which is included herein by reference. These photostabilizers are generally used in an amount of 0.05 to 10 wt.-% with respect to the total weigh of the topical sunscreen emulsion.

If present, the amount of the UV-filter substances (i.e. the sum of all UV-filter substances present in the cosmetic composition) is preferably selected in the range of 0.1 to 40 wt. %, more preferably in the range of 0.2 to 20 wt. % and most preferably in the range of 0.5 to 15 wt.-% based on the total weight of the cosmetic composition.

Particular advantageous compositions according to the present invention further comprise at least one UV-filter substance.

In a particular embodiment, the cosmetic compositions according to the present invention may further comprise at least one additional self-tanning agent which is preferably selected from the group consisting of mono- or polycarbonyl compounds, such as, for example, isatin, alloxan, ninhydrin, glyceraldehyde, mesotartaric aldehyde, glutaraldehyde, erythrulose, the pyrazoline-4,5-dione derivatives as described in FR-2,466,492 and WO97/35842, dihydroxyacetone (DHA) or the 4,4-dihydroxy-pyrazolin-5-one derivatives as described in EP-903,342. Preferably, DHA and/or erythrulose (in D- or L-form or as the racemate in particular erythrulose.

DHA can be used in the free form and/or in the encapsulated form, for example encapsulated in lipid vesicles, such as liposomes, which are described, in particular, in WO 97/25970.

The cosmetic compositions according to the present invention may also contain at least one synthetic or natural direct dye and/or at least one indole derivative, such as those described in EP-425,324 and EP-456,545 and/or at least one synthetic or natural agent for coloring the skin.

By the term "agent for coloring the skin" is intended any compound having a specific affinity for the skin and which imparts thereto a lasting and noncovering (namely, having no tendency to opacify the skin) coloring, which is removed neither with water nor using a solvent, and which withstands both rubbing and washing with a solution comprising surfactants. Such a lasting coloring is therefore distinguished from the superficial and short-lived coloring contributed, for example, by a makeup pigment.

The additional coloring agents can also be selected, for example, from among plant extracts, such as, for example, extracts of "insoluble" redwoods of the *Pzerocarpus* genus and of the *Baphia* genus, such as *Pzerocarpus santalinus, Pterocarpus osun, Plerocarpus soyauxii, Plerocarpus erinaceus, Pterocarpus indicus* or *Baphia nitida*, such as those described in EP-971,683.

The coloring agents can also be iron oxide nanopigments for which the mean size of the individual particles is less than 100 nm, such as those described in EP-966,953.

If present, the total amount of such additional self-tanning agent(s) in the compositions according to the invention is generally selected in proportions ranging from 0.1% to 20% by weight with respect to the total weight of the composition and preferably from 0.2% to 8% by weight with respect to the total weight of the composition.

Particularly preferred are cosmetic compositions which further comprise at least on ingredient selected from the group consisting of polysilicones-15, phenylbenzimidazol sulfonic acid, 3-benzylidene camphor, octocrylene, ethylhexyl methoxycinnamate, ethyl hexylsalicylate, homosalate, zinc oxide, bis-ethylhexyloxyphenol methoxyphenyl triazine, methylene bis-benzotriazolyl tetramethylbutylphenol, titanium dioxide, butyl methoxydibenzoylmethane, erythrulose, potassium cetyl phosphate, tocopherol and/or tocopherol acetate.

The cosmetic compositions according to the present invention may be in the form of a suspension or dispersion in solvents or fatty substances, or alternatively in the form of an emulsion or micro emulsion (in particular of oil-in-water (O/W) or water-in-oil (W/O) type, silicone-in-water (Si/W) or water-in-silicone (W/Si) type, PIT-emulsion, multiple emulsion (e.g. oil-in-water-in oil (O/W/O) or water-in-oil-in-water (W/O/W) type), pickering emulsion, hydrogel, alcoholic gel, lipogel, one- or multiphase solution or vesicular dispersion or other usual forms, which can also be applied by pens, as masks or as sprays.

If the cosmetic composition is an emulsion, such as in particular an O/W, W/O, Si/W, W/Si, O/W/O, W/O/W multiple or a pickering emulsion, then the amount of the oily phase present in such cosmetic emulsions is preferably at least 5 wt.-%, more preferably at least 10 wt.-%, such as in the range of 10 to 60 wt.-%, preferably in the range of 15 to 50 wt.-%, most preferably in the range of 15 to 40 wt.-%, based on the total weight of the cosmetic composition.

In one embodiment, the cosmetic compositions according to the present invention are advantageously in the form of an oil-in-water (O/W) emulsion comprising an oily phase dispersed in an aqueous phase in the presence of an O/W emulsifier. The preparation of such O/W emulsions is well known to a person skilled in the art.

If the cosmetic composition according to the invention is an O/W emulsion, then it contains advantageously at least one O/W- or Si/W-emulsifier selected from the list of, glyceryl stearate citrate, glyceryl stearate SE (self-emulsifying), stearic acid, salts of stearic acid, polyglyceryl-3-methylglycosedistearate. Further suitable emulsifiers are phosphate esters and the salts thereof such as cetyl phosphate (e.g. as Amphisol® A from DSM Nutritional Products Ltd.), diethanolamine cetyl phosphate (e.g. as Amphisol® DEA from DSM Nutritional Products Ltd.), potassium cetyl phosphate (e.g. as Amphisol® K from DSM Nutritional Products Ltd.), sodium cetearylsulfate, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, cetearyl glucoside, lauryl glucoside, decyl glucoside, sodium stearoyl glutamate, sucrose polystearate and hydrated polyisobutene. Furthermore, one or more synthetic polymers may be used as an emulsifier. For example, PVP eicosene copolymer, acrylates/C10-30 alkyl acrylate crosspolymer, and mixtures thereof.

The at least one O/W, respectively Si/W emulsifier is preferably used in an amount of 0.5 to 10 wt. %, in particular in the range of 0.5 to 6 wt.-%, such as more in particular in the range of 0.5 to 5 wt.-%, such as most in particular in the range of 1 to 4 wt.-%, based on the total weight of the cosmetic composition.

Particular suitable O/W emulsifiers to be used in the cosmetic compositions according to the invention encompass phosphate ester emulsifiers such as advantageously 8-10 alkyl ethyl phosphate, C9-15 alkyl phosphate, ceteareth-2 phosphate, ceteareth-5 phosphate, ceteth-8 phosphate, ceteth-10 phosphate, cetyl phosphate, C6-10 pareth-4 phosphate, C12-15 pareth-2 phosphate, C12-15 pareth-3 phosphate, DEA-ceteareth-2 phosphate, DEA-cetyl phosphate, DEA-oleth-3 phosphate, potassium cetyl phosphate, deceth-4 phosphate, deceth-6 phosphate and trilaureth-4 phosphate.

A particular suitable O/W emulsifier to be used in the cosmetic compositions according to the invention is potassium cetyl phosphate e.g. commercially available as Amphisol® K at DSM Nutritional Products Ltd Kaiseraugst.

Another particular suitable class of O/W emulsifiers are non-ionic self-emulsifying systems derived from olive oil e.g. known as (INCI Name) cetearyl olivate and sorbitan olivate (chemical composition: sorbitan ester and cetearyl ester of olive oil fatty acids) sold under the tradename OLIVEM 1000.

In one particular embodiment, the invention relates to cosmetic compositions with all the definitions and preferences given herein in the form of O/W emulsions comprising an oily phase dispersed in an aqueous phase in the presence of an O/W emulsifier wherein the O/W emulsifier is potassium cetyl phosphate. The amount of oily phase in such O/W emulsions is preferably at least 10 wt.-%, more preferably in the range of 10 to 60 wt.-%, most preferably in the range of 15 to 50 wt.-%, such as in the range of 15 to 40 wt.-%.

Particularly preferred are cosmetic compositions which further comprise at least on ingredient selected from the group consisting of polysilicones-15, phenylbenzimidazol sulfonic acid, 3-benzylidene camphor, octocrylene, ethylhexyl methoxycinnamate, ethyl hexylsalicylate, homosalate, zinc oxide, bis-ethylhexyloxyphenol methoxyphenyl triazine, methylene bis-benzotriazolyl tetramethylbutylphenol, titanium dioxide, butyl methoxydibenzoylmethane, erythrulose, potassium cetyl phosphate, tocopherol and/or tocopherol acetate.

The cosmetic compositions according to the invention in general have a pH in the range of 3 to 10, preferably a pH in the range of 4 to 8 and most preferably a pH in the range of 4 to 7.5. The pH can easily be adjusted as desired with suitable acids, such as e.g. citric acid, or bases, such as sodium hydroxide (e.g. as aqueous solution), triethanolamine (TEA Care), Tromethamine (Trizma Base) and Aminomethyl Propanol (AMP-Ultra PC 2000), according to standard methods in the art.

The invention is further illustrated with reference to the following, non-limiting examples, in which all percentages are by weight based on total weight unless otherwise specified.

EXPERIMENTAL PART

General Information

Abbreviations

AA amino acid
Ad adamantyl
Boc tert-butyloxycarbonyl
DCM dichloromethane
DIPEA N,N-diisopropylethylamine
DMAP N,N-dimethylaminopyridine
DMF dimethylformamide
Fmoc fluorenylmethoxycarbonyl
HPLC High Pressure Liquid Chromatography
IndEt 2-(1H-indol-3-yl)ethyl-
MeCN acetonitril
Naphala naphtylalanine Pbf 2,2,4,6,7-pentamethyldihydrobenzofuran-5-sulfonyl
Phe Phenylalanine
Pro proline
TBTU O-(Benzotriazol-1-yl)-N,N,N',N'-tetramethyluronium tetrafluoroborat
TCTU 2-(2-Pyridon-1-yl)-1,1,3,3-tetramethyluronium tetrafluoroborate
TFA trifluoroacetic acid
TIPS triisopropylsilane
Trp Tryptophan Preparative HPLC purifications: performed on a Waters High Performance Liquid Chromatography LC-2525 equipped with a Waters 2767 Sample Manager and a Waters FCII automated fraction collector, using a Grom Saphir 110 C18 10 μm 50×300 mm$^2$ preparative column and a Waters 2487 double wavelength UV-Vis detector operating at 220 and 254 nm.

$H_2O$+0.07% TFA (A" phase) and MeCN+0.07% TFA (B" phase) were used as eluents, with a flow of 55 mL/min.

1. Synthetic Strategies

Unsubstituted amides were prepared on rink linker amide resin using solid phase synthesis approach. After simultaneous cleavage of the side chain protecting groups as well as the attachment to the resin, the crude peptide is purified by preparative HPLC.

Substituted amides were prepared on 2-chloro trityl resin side as chain protected peptides with free acid and coupled with the corresponding amine to give the side chain protected test item in solution, which is deprotected and thoroughly purified by HPLC.

a. Preparation

Typical Procedure for the Preparation of the Free Amides

Approximately 2.5 g Fmoc-ramage-resin (loading approx. 0.5 mmol/g) is placed in a peptide synthesizer reaction tube and the sequence is assembled on a peptide synthesizer. 1.25 eq of the respective Fmoc-amino acids (side-chain functional groups may be Boc/Pbf/Trt) protected if present) are coupled to the growing peptide chain with 1.25 eq TBTU and 3 eq DIPEA. Fmoc protection group is removed with 4 methyl piperidine. The N-terminal Bz group is attached using 1.1 eq benzoyl chloride with a 5-fold excess of DIPEA.

The fully assembled peptide is cleaved from the resin with 25.8 ml of a TFA/TIPS/DCM=22.5/0.8/2.5 mixture (v/v). The crude peptide is precipitated by adding the solution to a 200 ml of IPE/Hexan=1/1 (v/v). The precipitate is directly purified by preparative HPLC resulting in the yields as given in table 2.

TABLE 2

| | Free amide peptides | |
|---|---|---|
| Entry | Sequence | Amount, yield |
| I-a | Bz-Gly-His-D-Phe-Arg-Trp-$NH_2$ *2TFA | 196 mg (19%) |
| I-b | Bz-Gly-His-D-Phe-Arg-D-2-NaphAla-$NH_2$ *2TFA | 351 mg (32%) |
| I-c | Bz-Gly-His-D-Phe-Arg-L-2-NaphAla-$NH_2$ *2TFA | 413 mg (39%) |
| I-g | Bz-Gly-His-D-Phe-Arg-D-Phe-$NH_2$ *2TFA | 218 mg (22%) |
| I-h | Bz-Gly-His-D-Phe-Dab-Trp-$NH_2$ *2TFA | 170 mg (14%) |
| I-i | Bz-Gly-His-D-Phe-Arg-(N-IndEt)Gly-$NH_2$ *2TFA | 135 mg, (13%) |

Typical Procedure for the Preparation of the Substituted Amides

Approximately 2 g 2-chloro-trityl-resin (loaded with the first amino acid approx. 0.5 mmol/g) is placed in a peptide synthesizer reaction tube and the sequence is assembled on a peptide synthesizer. 1.25 eq of the respective Fmoc-amino acids (side-chain functional groups are Boc/Pbf/Trt) protected if present) are coupled to the growing peptide chain with 1.25 eq TBTU and 3 eq DIPEA. Fmoc protection group is removed with 4 methyl piperidine. The N-terminal Bz group is attached using 1.1 eq benzoyl chloride with a 5-fold excess of DIPEA.

The fully assembled peptide is cleaved from the resin with three times 20 ml of DCM containing 0.1% TFA. The combined DCM portions are combined in a separatory funnel and washed neutral. Organic phase is dried over $Na_2SO_4$ and all volatile compounds removed in vacuum. Crude peptide is carefully coupled using 3 eq of 2,4,6-trimethyl-pyridine 1 eq of TPTU and 1.1 eq amine at 0° C. Regular aqueous workup ($NaHCO_3$, $KHSO_4$, NaCl) is followed by removal of all side chain protecting groups with TFA/TIPS/DCM=22.5/0.8/2.5 mixture (v/v) and precipitation by adding the solution to IPE/Hexan=1/1 (v/v). The precipitate is directly purified by preparative HPLC resulting in the yields as given in table 3.

TABLE 3

Substituted amide peptides

| Entry | Sequence | Amount, yield |
|---|---|---|
| I-d | Bz-Gly-His-D-Phe-Arg-D-Trp-N(Propyl)₂ *2TFA | 131 mg (12%) |
| I-e | Bz-Gly-His-D-Phe-Arg-Trp-N(Propyl)₂ *2TFA | 196 mg (36%) |
| I-f | Bz-Gly-His-D-Phe-Arg-Trp-NHOctyl *2TFA | 278 mg (28%) |
| R1 | Bz-Gly-D-His-D-Phe-Arg-Trp-N(Propyl)₂ *2TFA | 113 mg (10%) |
| R2 | Bz-Gly-His-Phe-Arg-Trp-N(Propyl)2 *2TFA | 176 mg (15%) |
| R3 | Bz-Gly-His-D-Phe-D-Arg-Trp-N(Propyl)₂ *2TFA | 214 mg (18%) |
| R4 | Bz-Gly-His-D-Phe-Arg-Tryptamide *2TFA | 40 mg (4%) |

3. MC1R Stimulation

Human MC1 Receptor Using cAMP HTRF Functional Assay:

Twenty seven (27) compounds were tested for agonist activity at the human MC1 receptor using cAMP HTRF (homogeneous time-resolved fluorescence) assays at eight (8) concentrations and in duplicate.

On the day of experimentation, compounds were tested at several concentrations in duplicate wells (n=2) to obtain a dose-response curve and an estimated EC50 value. Values obtained for the reference compound were compared to historical values obtained from the same receptor and used to validate the experimental session. For replicate determinations, the maximum variability tolerated in the test was of +/−20% around the average of the replicates.

Assay: After cultivation Chinese Hamster Ovary (CHO) cells were detached and incubated at a specific cell density in assay buffer. At this stage the CHO cells express the human MC1R at their surface. Agonist compounds were added at determined concentration and incubated for 30 min. Cells were lysed in detection buffer in order to extract cAMP. The amount of cAMP within the cells correlates with GPCR-activity, meaning that in this assay it correlates with MC1R-activity. cAMP was detected in a competitive HTRF assay for binding to an anti-cAMP-antibody.

TABLE 4

Results of the MC1R stimulation assay

| # | Name | EC50 [nM] |
|---|---|---|
| (I-a) | Bz-Gly-His-D-Phe-Arg-Trp-NH₂ *2TFA | 0.041 |
| (I-c) | Bz-Gly-His-D-Phe-Arg-L-2-NaphAla-NH₂ *2TFA | 0.11 |
| (I-b) | Bz-Gly-His-D-Phe-Arg-D-2-NaphAla-NH₂ *2TFA | 0.25 |

TABLE 4-continued

Results of the MC1R stimulation assay

| # | Name | EC50 [nM] |
|---|---|---|
| (I-d) | Bz-Gly-His-D-Phe-Arg-D-Trp-N(Propyl)₂ *2TFA | 0.42 |
| (I-e) | Bz-Gly-His-D-Phe-Arg-Trp-N(Propyl)₂ *2TFA | 0.88 |
| (I-f) | Bz-Gly-His-D-Phe-Arg-Trp-NHOctyl *2TFA | 1.06 |
| (I-g) | Bz-Gly-His-D-Phe-Arg-D-Phe-NH₂ *2TFA | 1.79 |
| (I-h) | Bz-Gly-His-D-Phe-Dab-Trp-NH₂ *2TFA | 7.51 |
| (I-i) | Bz-Gly-His-D-Phe-Arg-(N-Trp)Gly-NH₂ *2TFA | 4.4 |

REFERENCES

As references, various analogues of compounds formula (I) as outlined in table 3 have been prepared tested in the assay. As can be retrieved from table 5, these compounds showed significant lower activity.

TABLE 5

| # | Name | EC50 [nM] |
|---|---|---|
| R1 | Bz-Gly-D-His-D-Phe-Arg-Trp-N(Propyl)₂ *2TFA | 36 |
| R2 | Bz-Gly-His-Phe-Arg-Trp-N(Propyl)₂ *2TFA | 51.4 |
| R3 | Bz-Gly-His-D-Phe-D-Arg-Trp-N(Propyl)₂ *2TFA | 70.1 |
| R4 | Bz-Gly-His-D-Phe-Arg-Tryptamide *2TFA | 42.9 |

4. Ex-Vivo Skin Pigmentation Trial

Skin samples (from abdominal plastic surgery) have been cut in pieces of approx. 8×3 mm (Øx thickness) and were cultured up to day 6 in an air-liquid interface in a perforated ring of stainless steel in contact with a culture medium (modified Williams'E medium), the culture medium has been renewed every three days. Six skin specimens have been used for each treatment. Each test sample (4 µl/200 µM of active) has been applied topically on top of each piece after gentle cleaning of the surface with a cotton pad followed by covering with a 6 ø mm delivery membrane, which procedure has been repeated daily. After 6 days of incubation, the melanin amount was assessed on twelve skin sections for each treatment by staining using a modified Fontana-Masson stain. The amount of melanin present in each slide has been evaluated by estimating the intensity and the distribution of grey tone: 8-bit grey-scale images for each treatment have been captured at the microscope. Then the colour space of the images have been transformed from RGB into L*a*b* images and each pixel of the picture has been evaluated according to its L* values. The obtained results have been transformed in ranks of L* and then normalized on the ratio between the selected area and the area of the slide. The result is indicated as % increase versus untreated at day 6.

TABLE 5a skin pigmentation increase versus untreated

| # | Name | increase | SEM[+] | p-value[*] |
|---|---|---|---|---|
| (I-a) | Bz-Gly-His-D-Phe-Arg-Trp-NH₂ *2TFA | +18% | 3% | <0.01 |
| (I-d) | Bz-Gly-His-D-Phe-Arg-D-Trp-N(Propyl)₂ *2TFA | +21% | 6% | <0.05 |

[+]standard error of the mean
[*]calculated by Student's t-test for unpaired samples Cosmetic Composition Table 6 outlines exemplary O/W emulsions, wherein one compound selected from the group of (l-h) as outlined in table 1, is incorporated in the indicated amount.

TABLE 6

Exemplary O/W emulsion

| O/W Emulsions | 1 | 2 | 3 | 4 | 5 | 6 | 7 | 8 |
|---|---|---|---|---|---|---|---|---|
| Glyceryl Stearate | 2.5 | 2 | 1.2 | 1 | | | 1 | 1 |
| PEG-40 Stearate | 1 | | | | | | | |
| PEG-100 Stearate | | 2.5 | | | | | | 1 |
| Ceteareth-20 | | | | | 1 | | | |
| Glyceryl Stearate Citrate | | | | | | 0.5 | | |
| Potassium Cetyl Phosphate | | | | | | | 3 | 1.5 |
| Stearic Acid | | | 2.5 | 3 | | | | |
| Cetearyl Alcohol | 4 | | | 2 | | | 2 | |
| Stearyl Alcohol | | 2 | 1 | | | | | |
| Cetyl Alcohol | | | 1 | 1 | | | | 0.5 |
| Acrylates/$C_{10-30}$ Alkyl Acrylate Crosspolymer | | | | 0.2 | 0.2 | 0.4 | | 0.2 |
| Carbomer | 0.1 | | 0.2 | | | | | |
| Xanthan Gum | | 0.3 | | | | | | 0.3 |
| $C_{12-15}$ Alkyl Benzoate | 5 | | | 2 | 5 | 5 | 10 | 5 |
| Petrolatum | 5 | | 3 | | | | | |
| Butylene Glycol Dicaprylate/Dicaprate | | 4 | 2 | | 9 | | | 9 |
| Hydrogenated Polydecene | | | 3 | | 2 | | | 2 |
| Caprylic/Capric Triglyceride | 1 | 3 | | 5 | | 5 | 5 | |
| Cyclomethicone | | 5 | 2 | | | 10 | | |
| Methylpropanediol | 2 | | | | 3 | | | 3 |
| Glycerine | 4 | 7 | 3 | 4 | 3 | | 5 | 3 |
| Glyceryl Glucoside | 3.5 | 3 | 1 | 1 | 2 | | | 2 |
| Alcohol denat. | 1 | 3 | 0.5 | 10 | 4 | 8 | | 4 |
| Butylene Glycol | | | 3 | | | | | |
| Ascorbylglucoside | | 0.5 | | 1.0 | | 1.5 | | 0.1 |
| Ubiquinone (Coenzyme 10) | 0.1 | | 0.05 | | | | 0.01 | |
| Hyaluronic acid | | | | | 0.2 | | | |
| Bisabolol | 0.5 | | | | | | 0.2 | |
| Isotridecylsalicylate | | | 1 | 3 | 5 | 2 | 3 | 5 |
| Compound selected from the group of (I-a) to (I-i) | 0.001 | 0.25 | 0.0001 | 0.05 | 0.1 | 0.0003 | 0.03 | 0.002 |
| Dibutyl Adipate | 1.5 | 3 | | | | | | |
| Diisopropyl sebacate | | 1 | 1 | 2 | 3 | | | |
| Ethylhexyl Benzoate | | | | | | 0.75 | 1.5 | 1 |
| Titanium Dioxide (PARSOL TX) | | | 0.5 | 2 | | | | |
| Methylene Bis-Benztriazoyl Tetramethylbutylphenol | | | 0.5 | 4 | | 6 | | 2 |
| Ethylhexyl methoxycinnamate | | | | | 2 | | | |
| Phenylbenzimidazole Sulfonic Acid | | | | 2 | | 2 | 2 | |
| Butyl Methoxydibenzoylmethane | | | 1 | | 2 | 2 | 3 | 3 |
| Methylbenzylidene Camphor | | | | | 2 | 3 | | |
| Octocrylene | | 5 | | | | 2 | 10 | |
| Polysilicone-15 | | | | 2 | | 3 | | |
| Ethylhexyl Salicylate | | | | | 5 | | | |
| Homosalate | | | | 4 | 2 | | | |
| Bis-Ethylhexyloxyphenol Methoxyphenyltriazine | | 1.5 | | | | | | 2 |
| Silica | 1 | | 2.5 | | | 0.5 | | |
| Silica & Methicone | | | 4 | 1 | 2.5 | | | |
| Methyl Methacrylate Crosspolymer | | | | 1 | | | 2 | |
| Disodium EDTA | 0.1 | | | | | 0.5 | | |
| Fragrance, Preservatives | q.s. | | | | | | | |
| Sodium Hydroxide | q.s. | | | | | | | |
| Water | Ad 100 | | | | | | | |

The invention claimed is:

1. A compound or a cosmetically acceptable salt thereof, wherein the compound is selected from the group consisting of:

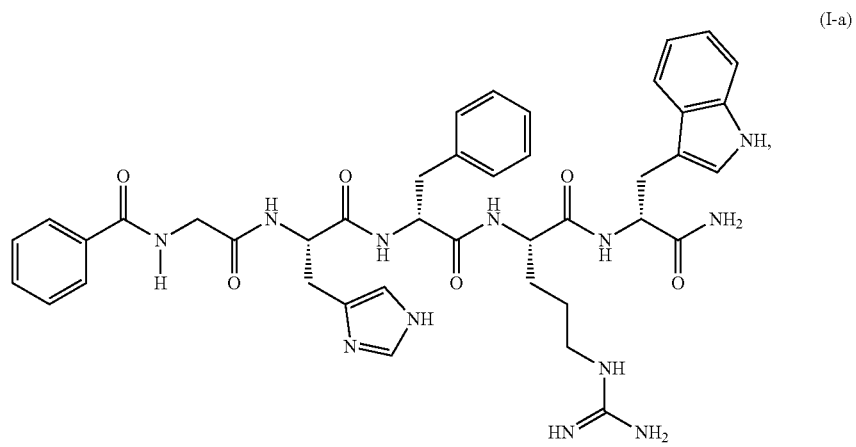
(I-a)
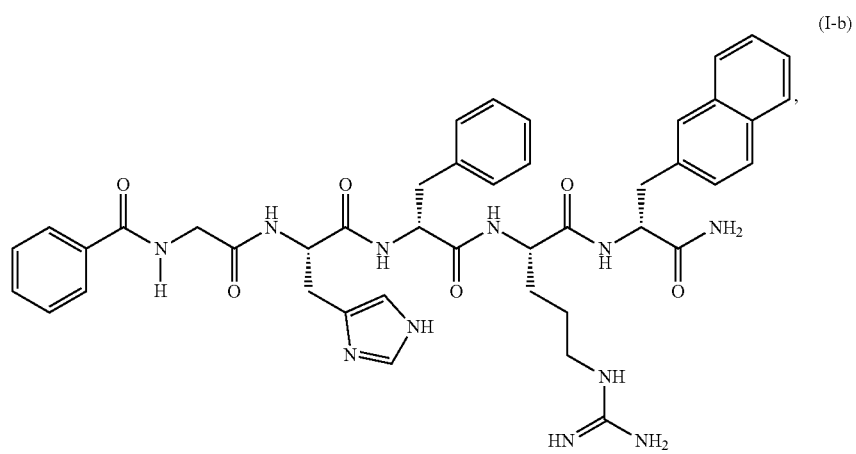
(I-b)
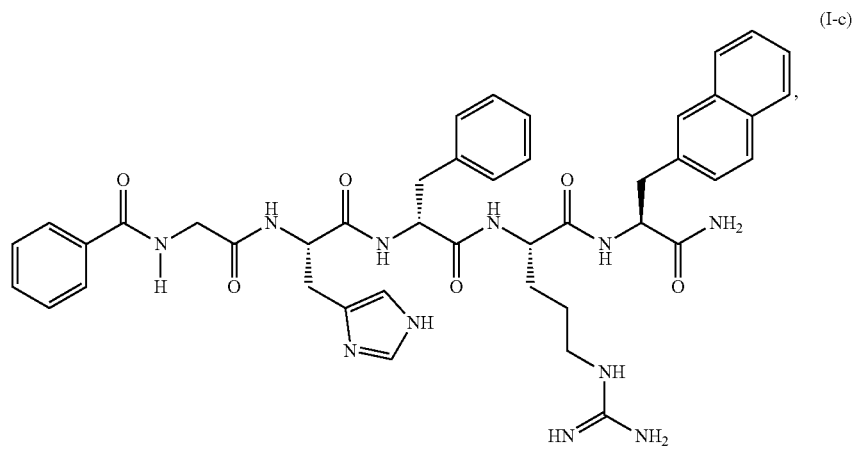
(I-c)

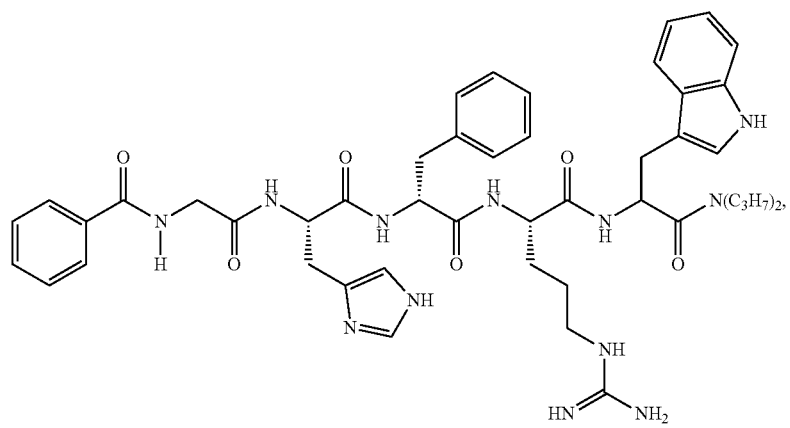
(I-d)
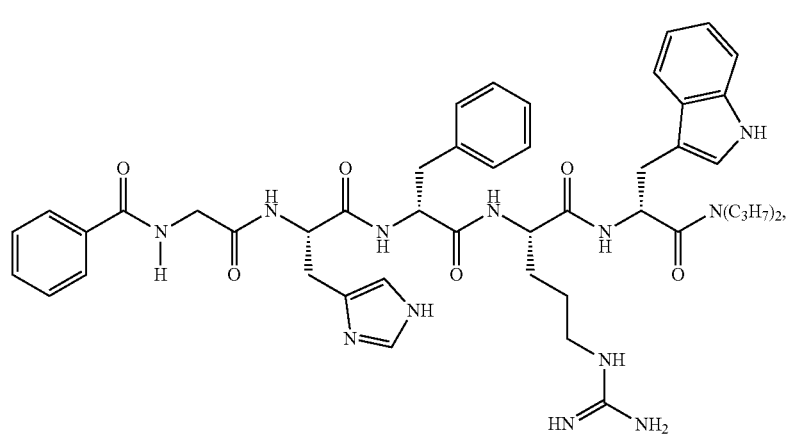
(I-e)
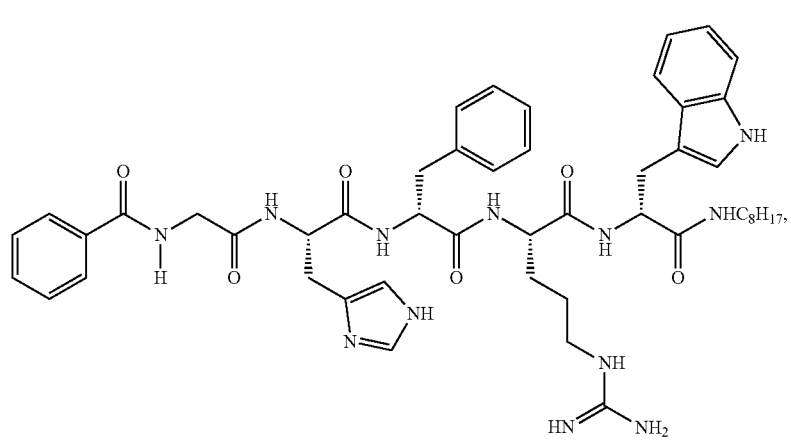
(I-f)
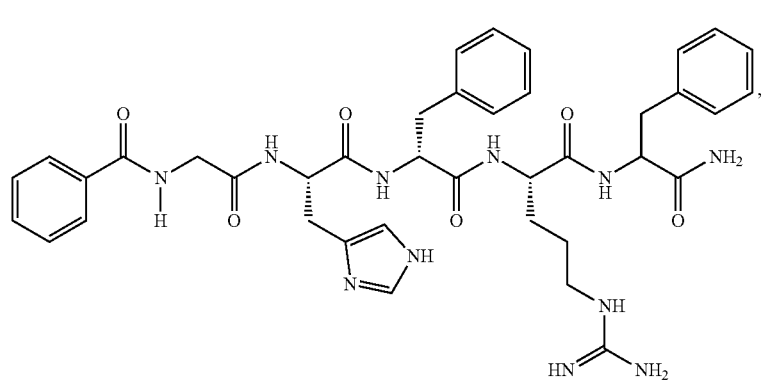
(I-g)

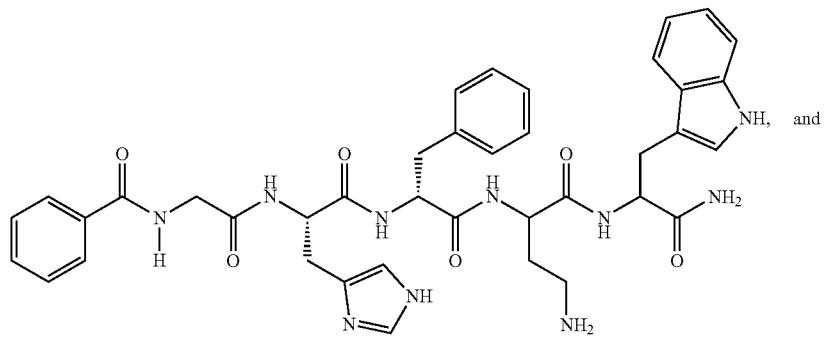

(I-h)

and

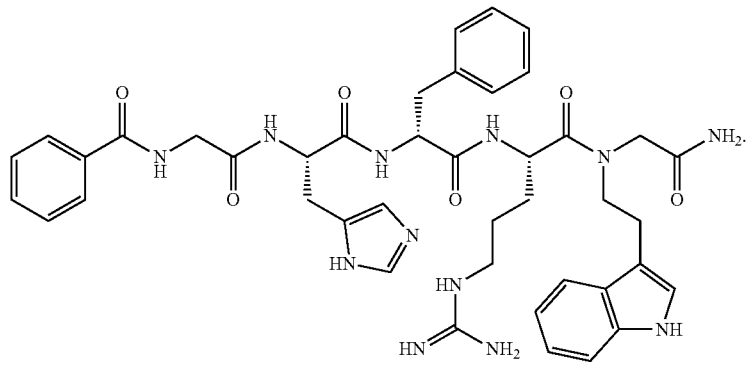

(I-i)

2. The compound according to claim 1, wherein the cosmetically acceptable salt is an acetate or a trifluoroacetate thereof.

3. A cosmetic composition comprising the compound of formulas (I-a) through (I-i) according to claim 1 or the cosmetically acceptable salt thereof and a cosmetically acceptable carrier.

4. The cosmetic composition according to claim 3, wherein the compound of formulas (I-a) through (I-i) or the cosmetically acceptable salt thereof is present in a total amount of about 0.00001 to 0.5 wt. %, based on the total weight of the cosmetic composition.

5. The cosmetic composition according to claim 3, wherein the compound of formulas (I-a) through (I-i) or the cosmetically acceptable salt thereof is present in a total amount of about 0.0001 to 0.25 wt. %, based on the total weight of the cosmetic composition.

6. The cosmetic composition according to claim 3, wherein the compound of formulas (I-a) through (I-i) or the cosmetically acceptable salt thereof is present in a total amount of about 0.0001 to 0.1 wt. %, based on the total weight of the cosmetic composition.

7. The cosmetic composition according to claim 3, wherein the cosmetic composition comprises at least one further ingredient selected from the group consisting of self-tanning agents, UV-filters, agents for the treatment of hyperpigmentation, agents for the prevention or reduction of inflammation, firming agents, moisturizing agents, soothing agents, energizing agents, agents to improve elasticity and agents to improve skin barrier properties.

8. The cosmetic composition according to claim 3, wherein the cosmetic composition comprises at least one further ingredient selected from the group consisting of polysilicones-15, phenylbenzimidazol sulfonic acid, 3-benzylidene camphor, octocrylene, ethylhexyl methoxycinnamate, ethyl hexylsalicylate, homosalate, zinc oxide, bis-ethylhexyloxyphenol methoxyphenyl triazine, methylene bis-benzotriazolyl tetramethylbutylphenol, titanium dioxide, butyl methoxydibenzoylmethane, erythrulose, potassium cetyl phosphate, tocopherol and tocopherol acetate.

9. A self-tanning or artificial/sunless tanning agent which comprises the compound of formulas (I-a) through (I-i) according to claim 1 or a cosmetically acceptable salt thereof.

10. A method for artificial/sunless tanning of human skin, enhancement of the natural glow of the skin, protection of skin against UV-radiation and/or prevention of photoage-induced skin structure defects, wherein the method comprises topically applying the cosmetic composition according to claim 3 to the skin of a subject in need thereof.

* * * * *